(12) United States Patent
Johns

(10) Patent No.: US 11,879,821 B2
(45) Date of Patent: *Jan. 23, 2024

(54) RHEOMETER AND METHOD FOR THE USE THEREOF

(71) Applicant: HAEMOGRAPH PTY LTD, Bayswater (AU)

(72) Inventor: William Richard Johns, Swansea (GB)

(73) Assignee: HAEMOGRAPH PTY LTD., Bayswater (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/856,250

(22) Filed: Jul. 1, 2022

(65) Prior Publication Data
US 2022/0404255 A1 Dec. 22, 2022

Related U.S. Application Data

(63) Continuation of application No. 16/346,854, filed as application No. PCT/GB2017/053393 on Nov. 10, 2017, now Pat. No. 11,378,507.

(30) Foreign Application Priority Data

Nov. 15, 2016 (GB) .................................. 1619337

(51) Int. Cl.
*G01N 11/08* (2006.01)
*G01N 33/49* (2006.01)
(Continued)

(52) U.S. Cl.
CPC .......... *G01N 11/08* (2013.01); *A61B 5/02035* (2013.01); *G01N 33/4905* (2013.01);
(Continued)

(58) Field of Classification Search
CPC .... G01N 11/08; G01N 33/4905; G01N 11/00; G01N 11/02; G01N 11/04; G01N 33/00;
(Continued)

(56) References Cited

U.S. PATENT DOCUMENTS 3,911,728 A 10/1975 Fixot
4,554,821 A 11/1985 Kiesewetter et al.
(Continued)

FOREIGN PATENT DOCUMENTS

JP S62194441 A 8/1987
JP 2007271323 A 10/2007
(Continued)

OTHER PUBLICATIONS

International Preliminary Report on Patentability for corresponding PCT Application No. PCT/GB2017/053393, dated May 31, 2019, 10 pgs.
(Continued)

*Primary Examiner* — Kristina M Deherrera
*Assistant Examiner* — Fatemeh Esfandiari Nia
(74) *Attorney, Agent, or Firm* — Shumaker & Sieffert, P.A.

(57) ABSTRACT

A device for determining the rheological properties of blood may include a channel having at least one channel sub-section that has a substantially constant cross-section; apparatus for determining a pressure differential along at least a portion of the sub-section of the channel; a first reservoir that is adapted to be located at a first end of the channel and to be placed in fluid communication with the channel, the first reservoir being of variable internal volume; a second reservoir that is adapted to be placed in fluid communication with first reservoir via the channel, the second reservoir being of variable internal volume; means for allowing blood to be introduced into the device; an outlet for allowing gas to be
(Continued)

expelled from the device; and means for varying the volume of the first reservoir.

15 Claims, 2 Drawing Sheets

(51) Int. Cl.
  *A61B 5/02* (2006.01)
  *G01N 33/487* (2006.01)
  *G01N 11/02* (2006.01)
  *G01N 33/483* (2006.01)
  *G01N 11/04* (2006.01)
  *G01N 33/00* (2006.01)
  *G01N 11/00* (2006.01)
  *G01N 33/48* (2006.01)

(52) U.S. Cl.
  CPC .............. *G01N 11/00* (2013.01); *G01N 11/02* (2013.01); *G01N 11/04* (2013.01); *G01N 33/00* (2013.01); *G01N 33/48* (2013.01); *G01N 33/483* (2013.01); *G01N 33/487* (2013.01); *G01N 33/49* (2013.01); *G01N 33/491* (2013.01)

(58) Field of Classification Search
  CPC .... G01N 33/48; G01N 33/483; G01N 33/487; G01N 33/49; G01N 33/491; A61B 5/02035
  See application file for complete search history.

(56) References Cited

U.S. PATENT DOCUMENTS

| | | | |
|---|---|---|---|
| 4,884,577 A | 12/1989 | Merrill | |
| 5,172,585 A | 12/1992 | Gleissle | |
| 6,386,016 B1 | 5/2002 | Gleissle | |
| 6,575,019 B1* | 6/2003 | Larson | G01N 11/08 73/54.04 |
| 6,581,440 B1 | 6/2003 | Rupieper et al. | |
| 6,907,772 B2 | 6/2005 | Kensey et al. | |
| 8,450,078 B2 | 5/2013 | Dennis et al. | |
| 9,594,023 B2* | 3/2017 | Tamada | G01J 3/44 |
| 2003/0182991 A1 | 10/2003 | Spaid et al. | |
| 2005/0087001 A1 | 4/2005 | Trani | |
| 2005/0213427 A1* | 9/2005 | Steckle | B01F 23/235 366/268 |
| 2008/0246945 A1 | 10/2008 | Heinzelmann et al. | |
| 2010/0139375 A1* | 6/2010 | Johns | G01N 33/4905 73/54.24 |
| 2012/0127466 A1* | 5/2012 | Karnes | G01N 33/2811 356/319 |
| 2012/0247190 A1 | 10/2012 | Brown et al. | |
| 2014/0296615 A1 | 10/2014 | Franano | |
| 2018/0015246 A1 | 1/2018 | Kanazawa et al. | |
| 2019/0070352 A1 | 3/2019 | Tsubouchi | |

FOREIGN PATENT DOCUMENTS

| | | |
|---|---|---|
| JP | 2016140433 A | 8/2016 |
| KR | 20120101251 A | 9/2012 |
| KR | 1020130107119 A | 10/2013 |
| KR | 101580644 B1 | 12/2015 |
| WO | 2008099179 A2 | 8/2008 |
| WO | 2011051706 A1 | 5/2011 |

OTHER PUBLICATIONS

International Search Report and Written Opinion dated Jan. 29, 2018 from counterpart international Application No. PCT/GB2017/053393, 14 pp.

Narayanan, "dual chamber capillary viscometer", Review of Scientific Instruments, AIP, Melville, NY, US, vol. 57, No. 6, Jun. 1, 1986 (Jun. 1, 1986), p. 1182-1184, XP002087597.

Prosecution History from U.S. Appl. No. 16/346,854, now issued U.S. Pat. No. 11,378,507, dated Apr. 16, 2021 through Apr. 15, 2022, 100 pp.

Search Report under Section 17 dated Apr. 6, 2017 from counterpart GB Application No. 1619337.7, 4 pp.

Translation of Office Action from counterpart Japanese Application No. 2019-524941 dated Jul. 14, 2021, 7 pp.

* cited by examiner

RHEOMETER AND METHOD FOR THE USE THEREOF

This application is a continuation of U.S. patent application Ser. No. 16/346,854, filed May 1, 2019 and now issued as U.S. Pat. No. 11,378,507 B2, which is a national stage entry under 35 U.S.C. § 371 of International Application No. PCT/GB2017/053393, filed Nov. 10, 2017, which claims the benefit of GB Application No. 1619337.7, filed Nov. 15, 2016, the entire content of all being incorporated herein by reference.

TECHNICAL FIELD

The present disclosure relates to a device for determining the rheological properties of non-Newtonian fluids, in particular to a device for determining the rheological properties of blood, and to a method for the use thereof.

BACKGROUND

It is often desirable to obtain a rapid evaluation of the rheological properties of a patient's blood. Knowledge of such rheological properties is of value in assessing the administration of coagulants and anticoagulants to patients. It may also predict the likelihood of a bleed or thrombotic event in those that have a propensity to bleed or are at increased risk of clotting. Further situations in which it is important to know the rheological properties of blood include monitoring patients during surgery and during the reversal of anti-coagulation following surgery. Changes in blood rheology also occur in patients with sepsis and may provide an early indication that the condition is present. If sepsis is detected sufficiently early, treatment for the condition may be relatively straightforward.

Similarly, during the administration of anti-coagulants or the reversal of blood anti-coagulation following surgery, it would be very useful to have access to timely feedback on changes in the rheological properties of blood.

However, current tests for determining the rheological properties of blood tend to be time-consuming and require that a volume of blood is withdrawn from the patient and sent to a specialist bench-mounted instrument, such as a thromboelastograph, for analysis. Thus, there is a need for a simple bedside instrument that can be used more routinely.

In the following description the term blood encompasses and refers to human blood and to animal blood and can also mean blood and blood products.

SUMMARY

The present disclosure may provide a device for determining the rheological properties of blood, the device comprising two reservoirs, each having a variable internal volume and being adapted to be placed in fluid communication with the other via a channel. Blood may be caused to flow along the channel by altering the internal volumes of the two reservoirs. The channel includes one or more sections each having a substantially uniform cross section. Where there are two or more uniform sections each section differs in cross sectional area from other sections. The device is provided with a pressure gauge or pressure sensors for determining a pressure differential along at least a portion of the channel that has a substantially uniform cross-section.

Information about the rheology of the liquid blood may be obtained by determining the pressure differentials across a number of sections of differing cross-sectional area resulting from a given flow rate. Alternatively, information about the rheology of the blood may be obtained by determining the pressure differential across a section of substantially uniform cross section at a number of different defined flow rates.

Thus, the device is based on a simple, alternating direction pumping system that does not require large volumes of blood in order to be able to function. Other pumping systems used in previous devices such as that described in WO 2011/051706 are less advantageous. For example, peristaltic pumping systems may damage suspended components in the liquid (e.g. the blood cells present in a blood sample) through the compression of the tube containing the liquid. Centrifugal pumping systems are not practicable for small volumes of liquid. Additionally, flow rates from a centrifugal or peristaltic pump may be difficult to monitor, leading to the need for an additional component (a flowmeter) within the device. The flow rate from a reservoir having a variable internal volume is accurately determined by its rate of change in volume.

The device of the present disclosure allows liquid to be pumped in alternating directions along the channel, such that certain artefacts in the measurements, due for example to slight non-uniformities in the tubing, will tend to cancel each other out. Pumping liquid in alternating directions may allow more complex analyses to be performed, such as the measurement of the oscillatory fluid response with properties such as the viscous and elastic moduli.

In a first aspect, the present disclosure may provide a device for determining the rheological properties of a non-Newtonian fluid, such as blood, the device comprising:
  a channel having at least one channel sub-section that has a substantially constant cross-section;
  apparatus for determining a pressure differential along at least a portion of the sub-section of the channel;
  a first reservoir that is adapted to be located at a first end of the channel and to be placed in fluid communication with the channel, the first reservoir being of variable internal volume;
  a second reservoir that is adapted to be placed in fluid communication with first reservoir via the channel, the second reservoir being of variable internal volume;
  means for allowing blood to be introduced into the device;
  an outlet for allowing gas to be expelled from the device; and
  means for varying the volume of the first reservoir, such that when the first and second reservoirs are in fluid communication with the first and second ends of the channel respectively, blood may be caused to flow along the channel in alternating directions.

The at least one channel sub-section may be straight or curved.

In a second aspect, the present disclosure may provide a device for determining the rheological properties of blood, the device comprising:
  a channel having at least one channel sub-section that has an increasing or decreasing cross-section, preferably a uniformly increasing or decreasing cross-section;
  apparatus for determining a pressure differential along at least a portion of the sub-section of the channel;
  a first reservoir that is adapted to be located at a first end of the channel and to be placed in fluid communication with the channel, the first reservoir being of variable internal volume;
  a second reservoir that is adapted to be placed in fluid communication with first reservoir via the channel, the second reservoir being of variable internal volume;
  means for allowing blood to be introduced into the device;

an outlet for allowing gas to be expelled from the device; and means for varying the volume of the first reservoir, such that when the first and second reservoirs are in fluid communication with the first and second ends of the channel respectively, blood may be caused to flow along the channel in alternating directions.

The at least one channel sub-section may be straight or curved.

The at least one channel sub-section may have a cross-section that increases or decreases in a non-uniform manner, for example, the cross-section may increase in a semi-hyperbolic manner or follow sinusoidal variations.

Thus in both the first and second aspects of the disclosure, when the first and second reservoirs are in fluid communication with each other via the channel, blood may be caused to flow in either direction along the channel by altering the internal volume of the first and/or second reservoir. Both the first and second aspect take the same approach to providing a device that can measure the rheological properties of blood. For the device according to the second aspect of the present disclosure alternating flow through such a non uniform channel can furnish additional information on the elastic properties of a viscoelastic fluid such as blood. Such tapered sections can all taper in the same direction within a channel or some can taper in opposing directions.

Typically, in the device according to the first or second aspect of the present disclosure the first reservoir is a syringe, that is, it comprises a plunger and a hollow cylinder, the plunger being movable along the longitudinal axis of the cylinder to alter the internal volume of the reservoir. The syringe may be used to obtain a blood sample from a patient and may subsequently be placed in fluid communication with the channel. In this case, the syringe provides the means for allowing liquid to be introduced into the device. After testing, the syringe may be removed from the device to allow the blood sample to be used in other tests.

Typically, the device also comprises means for varying the volume of the second reservoir, such that when the first and second reservoirs are in fluid communication with each other, fluid may be caused to flow along the channel by varying the volume of the second reservoir. Typically, the second reservoir is also a syringe.

In other embodiments, the reservoir may be provided by a flexible casing, e.g. an elastic bulb.

In certain embodiments, the second reservoir comprises compressible portions located internally so as to provide the reservoir with a variable internal volume. The compressible portions may be, for example, air pockets or resiliently-deformable inserts.

In general, the channel of the device according to the first aspect of the disclosure has a plurality of sub-sections, each sub-section having a substantially constant cross-section and being provided with a respective differential pressure apparatus for determining a pressure differential across at least a portion of that sub-section, the sub-sections being of different cross-sections.

In this case, rheological properties of the liquid may be determined from the pressure readings obtained from the plurality of sub-sections. Each sub-section determines an apparent viscosity, which for a non-Newtonian fluid such as blood, will differ from sub-section to sub-section. The rheological properties may be derived from the relationship between the apparent viscosity and the strain rate in each of the sub-sections.

In the event that the alternating flow is not a simple forward and reverse flow, rheological properties related to the viscosity, such as an apparent complex modulus, may be derived by relating the transient pressure to the transient flowrate.

In the case that only one sub-section is present, it may be necessary to carry out tests at different flow rates in order to determine the rheological properties of the blood. Different flow rates produce different strain rates, and hence for non-Newtonian fluids, different apparent viscosities. Thus, rheological properties of the liquid may be determined from the relationship between the apparent viscosity and the strain rate.

The apparatus for determining a differential pressure may be a pressure monitoring system. The pressure monitoring system may be electronically or physically monitored for real time or subsequent processing and analysis. For example, the pressure sensors may be piezo-resistive strain gauges or may be capacitive sensors sensing the deformity of the channels through which the fluid flows.

In the case that more than one sub-section is provided, the sub-sections may all be aligned with each other. The channel may be made of disposable plastic tubing incorporating the requisite sections. The tubing may be rigid or flexible. It may be fitted into a straight outer channel into which it can be easily inserted and from which it can be easily removed. Alternatively, a lower plate may be provided with a channel formed in its upper surface into which the plastic tubing of the channel can be fitted and then clamped in place, for example, by an upper or supplementary plate. The plastic tubing may be formed as an integral part of the upper plate, with pressure sensors incorporated into the lower plate. In this way the upper plate, through which blood passes, may be an inexpensive disposable part, with the more expensive, non disposable portion including sensors and electrical components incorporated into the lower plate. This may help to provide a more compact device. Overall, care should be taken in the design to avoid sharp changes in direction that could damage or trap the fluid.

Typically, the internal diameter of the at least one sub-section is greater than 150 mm, preferably greater than 200 micron, more preferably greater than 300 micron. Typically, the internal diameter of the at least one sub-section is less than 3000 micron, preferably less than 2000 micron, more preferably less than 1000 micron.

Preferably, the at least one sub-section has a circular cross-section.

Typically, the length of the at least one sub-section is greater than 0.5 cm, preferably greater than 1 cm. Typically, the length of the at least one sub-section is less than 30 cm, preferably less than 15 cm, more preferably less than 10 cm.

Typically, the ratio of length to internal diameter of the at least one sub-section is greater than 5:1, preferably greater than 10:1, more preferably greater than 20:1.

Typically, the distance between the first and second reservoirs, when they are in fluid communication with each other via the channel, is less than 30 cm, preferably less than 20 cm.

Typically, the first and second reservoirs each have a maximum volume that is less than 50 ml, preferably less than 40 ml, more preferably less than 30 ml. Preferably a standard syringe size of 1 ml, 3 ml, 5 ml, 10 ml, 20 ml or 30 ml is used.

In certain embodiments, the device according to the first or second aspects of the disclosure may comprise means for imposing a pre-determined flow rate on the blood (that is, the device may function as a strain-controlled rheometer). In other embodiments, the device according to the first or second aspects of the disclosure may comprise means for imposing a pre-determined pressure differential on the blood (that is, the device may function as a stress-controlled rheometer).

In a third aspect, the present disclosure may provide a device for determining the rheological properties of blood, the device comprising:
  a channel;
  an apparatus for determining a pressure differential along at least a portion of the channel;
  a first reservoir that is adapted to be located at a first end of the channel and to be placed in fluid communication with the channel, the first reservoir being of variable internal volume;
  a second reservoir that is adapted to be placed in fluid communication with first reservoir via the channel, the second reservoir being configured to hold a liquid received from the channel, such that the liquid may be returned to the channel;
  means for allowing blood to be introduced into the device;
  an outlet for allowing gas to be expelled from the device; and
  means for varying the volume of the first reservoir, such that when the first and second reservoirs are in fluid communication with the first and second ends of the channel respectively, blood may be caused to flow along the channel in alternating directions.

The channel may have one or more of the features of the channel of the device according to the first or second aspects of the disclosure.

The first reservoir may have one or more of the features of the first reservoir of the device according to the first or second aspects of the disclosure.

In a fourth aspect, the present disclosure may provide a method of measuring the rheological properties of blood, comprising the steps of:
  providing a device according to the first aspect of the disclosure;
  introducing blood into the device;
  expelling gas or fluid from the device;
  ensuring that the first and second reservoirs are in fluid communication with the channel;
  altering the internal volume of the first reservoir so as to cause blood to flow along the channel in a first direction, between the first and second reservoirs;
  recording or measuring the rate of blood flow between the first and second reservoirs; and
  monitoring the apparatus for determining a pressure differential along at least a portion of the at least one sub-section having substantially uniform cross section; and
  causing the blood to flow along the channel in a second direction.

In general, the method comprises the step of causing liquid to flow along the channel in a second direction. By taking measurements in both flow directions and averaging them (or using more advanced signal processing techniques such as Fourier Transforms or FFT), it may be possible to reduce measurement errors and/or reduce the need for precise mounting of the device on a stable surface.

The method may be carried out e.g. by imposing a known flow rate on the blood and monitoring the associated pressure differential. Alternatively, the method may be carried out by imposing a known pressure differential and measuring the associated flow rate.

Preferably, the blood is made to cycle a plurality of times between the first and second reservoirs. Forward and reverse flow cycles may be undertaken for a small number of cycles to measure the rheological properties of the fluid at a defined point in time, or may be continued for a protracted period, in order to monitor changes in rheological behaviour, for example, due to clotting or gelling of the fluid.

In the case that the channel has a plurality of sub-sections each having a respective cross section different from the other sub-sections, testing may be carried out at a constant flow rate or a periodic flow with a single amplitude and frequency.

In the case the that channel has a single sub-section, it may be necessary to carry out tests at different flow rates in order to impose different strain rates on the test liquid. Alternatively, if it is only desired to monitor the progress of clotting or gelling of the test liquid, the flow rate may be held constant or may be the same in successive cycles.

The liquid may be a blood sample. In this case, the method may comprise the step of providing a syringe containing a blood sample, and placing the syringe in fluid communication with the channel such that the syringe functions as the first reservoir. In this way, the step of transferring the blood sample from the syringe to a separate reservoir provided by the measurement device may be avoided, thus reducing the level of skill required to operate the device, as well as the delay in testing the sample.

Preferably, the method includes the step of calibrating the device. This is typically done through the steps of:
  introducing a Newtonian fluid of known viscosity (for example, water) into the device;
  expelling gas from the device;
  ensuring that the first and second reservoirs are in fluid communication with each other via the channel;
  altering the internal volume of the first reservoir so as to cause liquid to flow along the channel in a first direction, between the first and second reservoirs; and
  monitoring the pressure apparatus to determine the pressure difference along the least one sub-section.

Calibration of the device using a Newtonian fluid of known viscosity may allow the device to be manufactured to less exacting engineering tolerances. That is, the requirement for precision engineering of the device is reduced, since the rheological properties of the blood sample (which can be used as a test liquid) may be calculated in relation to the known properties of the calibration fluid, rather than being calculated directly from the dimensions of the device. Thus the apparent viscosity of the blood can be calculated from the following formula which does not include explicit reference to the tube diameter or the distance between the pressure sensor points:

$$\mu/\mu_C = \Delta P G_C / (\Delta P_C G)$$

In the above formula, $\mu$ is (apparent) viscosity, $G$ is volumetric flow rate, and $\Delta P$ is pressure difference. Subscript 'C' refers to the Newtonian calibration liquid. Typically, the step of calibrating the device comprises causing the calibration liquid to cycle repeatedly from the first reservoir to the second reservoir and back.

It is preferable that the volume discharged at each stroke is less than the complete volume of the reservoir because discharging the final 10% to 20% of the volume places the red blood cells under stress that may cause them to rupture causing haemolysis. The stress arises both from the high strain rates caused by the high radial velocities and by the plunger closing against the end of the syringe. The radial velocities occur when the blood at the circumference of the piston is driven to the axis, where the streamlines turn through 90 degrees for the blood to exit through the axially located tubing or channel. Then when the plunger end of the syringe strikes the end of the syringe body it directly crushes any red cells remaining in the reservoir.

In one embodiment the internal volume is reduces by not more than 80% within the first 10 seconds. Higher discharge rates may damage liquids such as blood.

In certain cases blood is caused to flow in alternating directions along the channel for at least 5 minutes. This may allow changes in the rheology of the blood to be monitored, such as those caused by clotting. Typically, the period of each individual flow cycle is in the range 1-120 s, preferably in the range 10-120 s.

The device used in the method according to the fourth aspect of the disclosure may have one or more of the optional features of the device according to the first or second aspect of the disclosure, whether taken alone or in combination.

BRIEF DESCRIPTION OF THE DRAWINGS

The disclosure will now be described by way of example with reference to the following Figures.

DETAILED DESCRIPTION

Figure 1:
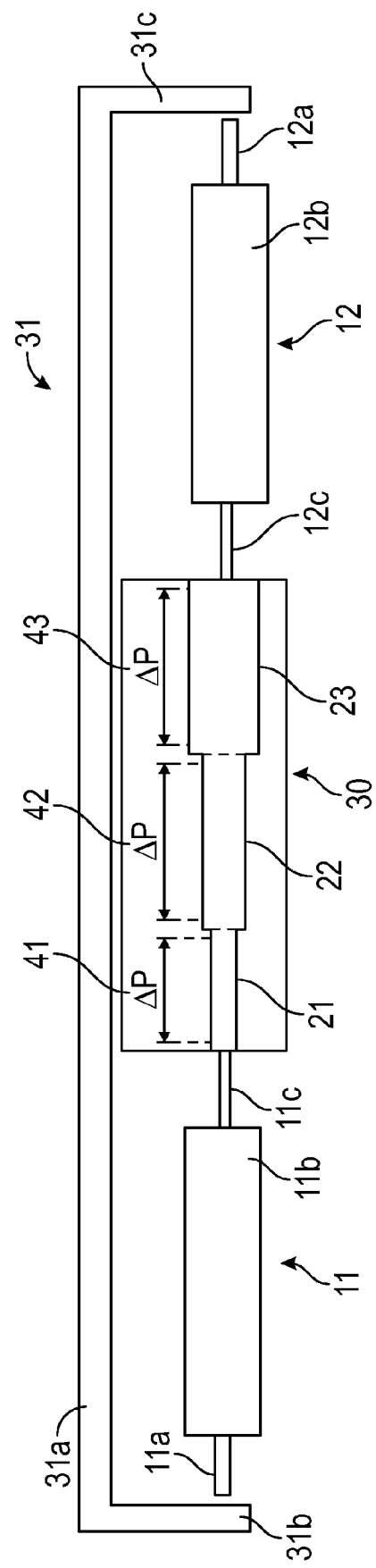
FIG. 1 shows a schematic plan view of a device for determining the rheological properties of blood, according to an embodiment of the first aspect of the disclosure.

Referring to FIG. 1, a block 30 comprises a plurality of channels 21, 22, 23, each channel having a circular internal cross-section. Each channel 21, 22, 23 has a different internal diameter in the range 200-2000 micron. The channels are each 1-15 cm in length and have a length:internal diameter ratio in the range 10:1 to 40:1. The channels are arranged in series so as to provide a fluid flow path between opposite ends of block 30. Each channel is provided with means of monitoring the respective pressure differentials. In the illustrated embodiment each channel is provided with tappings for a respective differential pressure gauge 41, 42, 43.

A first syringe 11 comprises a plunger 11a and a hollow cylinder 11b and a hollow connector 11c. The plunger is movable along a longitudinal axis of the cylinder. The connector is aligned with the longitudinal axis of the cylinder and is in fluid communication with the cylinder.

The connector 11c is reversibly engaged with channel 21, so as to provide a fluid flow path between the cylinder and channel 21. Thus the plunger 11a is movable relative to cylinder 11b, connector 11c, and block 30.

A second syringe 12 comprises a plunger 12a, a hollow cylinder 12b and a hollow connector 12c that is reversibly engaged with hollow cylinder 12b. The plunger is movable along a longitudinal axis of the cylinder. The connector is aligned with the longitudinal axis of the cylinder and is in fluid communication with the cylinder.

The connector 12c is engaged with channel 23 and provides a fluid flow path between channel 23 and cylinder 12b. Thus, plunger 12a is movable relative to cylinder 12b, connector 12c and block 30.

The first and second syringes each have an internal volume of about 5-20 ml.

Driving element 31 has an elongate central portion 31a and side arms 31b, 31c extending laterally from each end of the central portion. Side arm 31b is configured to urge against plunger 11a of the first syringe, while side arm 31c is configured urge against plunger 12a of the second syringe. Driving element 31 is electronically controlled.

In use, first syringe 11 is provided with a sample of a Newtonian liquid of known viscosity, which is held within the hollow cylinder 11b. The connector 11c is brought into engagement with channel 21 so as to provide a fluid flow path from the hollow cylinder 11b to channel 21. Hollow cylinder 11b is then clamped into place relative to block 30.

The second syringe 12 is arranged such that the plunger 12a is fully depressed and connector 12c is temporarily disengaged from cylinder 12b.

Side arm 31b is urged against plunger 11a so as to cause the liquid to flow out of cylinder 11b and through hollow connector 11c, channels 21, 22, 23 and hollow connector 12c. Any gas present within the first and second syringes and channels 21, 22, 23 is expelled via hollow connector 12c of the second syringe, after which hollow cylinder 12b is re-engaged with hollow connector 12c and clamped into place.

Driving element 31 is then activated so as to urge side arm 31a further against plunger 11a of the first syringe 11. This causes the liquid to be discharged from syringe 11 and forced through channels 21, 22, 23 so that the second syringe 12 becomes charged with the liquid. Consequently, the internal volume of the second syringe increases and plunger 12a is urged away from block 30.

The pressure drop across each channel 21, 22, 23 is measured during the motion. When syringe 11 is fully discharged, the motion of driving element 31 is reversed and pressure drop measurements are taken with flow in the opposite direction. The velocity of movement in both directions is accurately controlled and recorded. The velocity is the same in both directions. The cycle is repeated a sufficient number of times to ensure that accurate and reproducible pressure drop readings are recorded. These measurements are calibration measurements. They can be taken immediately before tests on blood or can be undertaken at initial assembly so that each block 30 is pre-calibrated.

In use, a cycle similar to the calibration cycle is undertaken, but using a blood sample in syringe 11. The forward and reverse flow cycle may be undertaken for a small number of cycles to measure the initial rheological properties of the blood, or may be continued for a protracted period (for example, up to half an hour) to track changes in the rheological properties of the blood as it clots.

It is advisable to maintain the device at a fixed orientation during use (for example, block 30 may extend in a generally horizontal direction or a generally vertical direction). This will help to reduce potential inaccuracies arising from changes in the pressure exerted by the weight of the liquid itself. However, due to the relatively small amount of liquid in the device, it is not anticipated that these effects will be very significant.

The device is either maintained at an accurately controlled temperature or insulated to maintain a substantially constant temperature, which is measured. This allows the results to be corrected for the variation of rheological properties with temperature.

Figure 2:
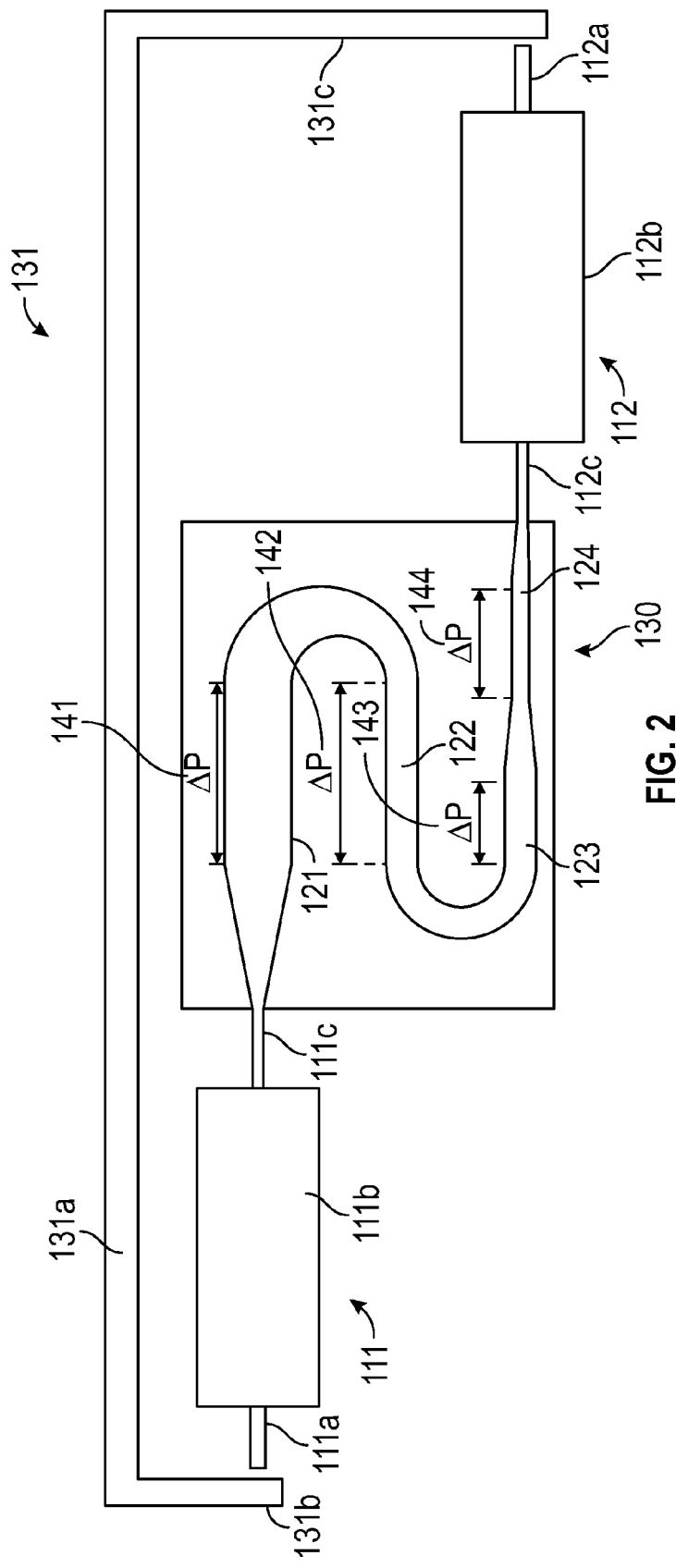
FIG. 2 shows a schematic plan view of a device for determining the rheological properties of blood including a channel that alternates in direction, according to another embodiment of the first aspect of the disclosure.

In the embodiment shown in FIG. 1, the channels 21, 22, 23 are all aligned along the same axis. However, in other embodiments the channels may be arranged such that liquid flowing along a pair of adjacent channels initially travels generally in a direction from the first syringe towards the second syringe, but changes course at the junction between the adjacent channels so as to travel generally in a direction from the second syringe towards the first syringe. Such configurations may allow a more compact device to be provided. This is illustrated in FIG. 2.

In the embodiment shown in FIG. 1, the channels 21, 22, 23 are formed within block 30. However, other embodiments are envisaged in which the channels are provided by tubes of different diameters or by a single tube having sections of different diameter. Tapered tubes are also envisaged.

It should be emphasised that although FIG. 1 shows a device having three channels, other embodiments are possible that have a greater or lesser number of channels. The present disclosure does not require that the channels be placed in any particular sequence in terms of their internal diameters. A mechanically simpler embodiment requires just a single channel having a substantially constant cross-section. In this case, differing strain rates are achieved by altering the forward and backward velocity of the driving element 31 from cycle to cycle.

The connecting tubes between the syringes and the block may be replaced by a direct connection such as a standard Luer lock thereby simplifying the set up and reducing the volume of blood between the syringe and the block.

In the embodiment shown in FIG. 2 an alternative arrangement is shown incorporating a channel that alternates in direction in order to reduce the maximum linear dimension of the device. The operation and use of the arrangement shown in FIG. 2 is as for the embodiment shown in FIG. 1 and as for the calibration cycle described above, in which the sections corresponding to FIG. 1 are numbered on and incremented by 100.

Therefore referring to FIG. 2, a block 130 comprises a plurality of channels 121, 122, 123, each channel having a circular internal cross-section. Each channel 121, 122, 123 has a different internal diameter in the range 200-2000 micron. The channels are each 1-15 cm in length and have a length:internal diameter ratio in the range 10:1 to 40:1. The channels are arranged in series in a snake like arrangement so as to provide a fluid flow path between opposite ends of block 130 with a reduction in the linear extent of the device. Each channel is provided with means of monitoring the respective pressure differentials. In the illustrated embodiment each channel is provided with tappings for a respective differential pressure gauge 141, 142, 143.

A first syringe 111 comprises a plunger 111a and a hollow cylinder 111b and a hollow connector 111c. The plunger in the same way as in the arrangement shown in FIG. 1, is movable along a longitudinal axis of the cylinder. The connector is aligned with the longitudinal axis of the cylinder and is in fluid communication with the cylinder.

The connector 111c is reversibly engaged with channel 121, so as to provide a fluid flow path between the cylinder and channel 121. Thus the plunger 111a is movable relative to cylinder 111b, connector 111c, and block 130.

A second syringe 112 comprises a plunger 112a, a hollow cylinder 112b and a hollow connector 112c that is reversibly engaged with hollow cylinder 112b. The plunger is movable along a longitudinal axis of the cylinder. The connector is aligned with the longitudinal axis of the cylinder and is in fluid communication with the cylinder.

The connector 112c is engaged with channel 123 and provides a fluid flow path between channel 123 and cylinder 112b. Thus, plunger 112a is movable relative to cylinder 112b, connector 112c and block 130.

The first and second syringes each have an internal volume of about 5-20 ml.

Driving element 131 has an elongate central portion 131a and side arms 131b, 131c extending laterally from each end of the central portion. Side arm 131b is configured to urge against plunger 111a of the first syringe, while side arm 131c is configured urge against plunger 112a of the second syringe. Driving element 131 is electronically controlled.

In use, the calibration and operation functions of the first syringe 111 and the second syringe 112 is as set out for the device according to the first aspect of the present disclosure with syringe 11 and 12.

It may also be advantageous for the embodiments of both FIG. 1 and FIG. 2 to divide the instrument through the plane of the channel, so that all sensors, electrical and electromechanical parts are in one section, a lower section or portion. The other section of the division, the upper portion or section, may consist of tubing that is slotted into channels of semi-circular cross section and clamped in place. Alternately, the upper section may consist of a plate incorporating channels (or tubing) of circular cross section that slot into channels of semi circular cross section incorporated in the lower section. The upper section may be disposable after use. In either of these alternatives, pressure sensors in the lower section may sense the pressure in the tubing or channel without contacting the fluid. As a further alternative, pressure sensors may be incorporated in tubing with electrical connections to the lower section.

Various modifications may be made to the described embodiment without departing from the scope of the present disclosure, for example other alternatives and options may be envisaged within the scope of the claims, for example the driving element 31 may be replaced by a clamp on the plunger 11a so that the plunger is driven in and withdrawn at one end. The plunger 12a then moves back and forth in response to the pressure in the fluid exerted on the plunger.

The flow actuator and pressure monitoring apparatus or monitoring system may be connected to an electronic system for processing the signals and recording and/or displaying relevant rheological information, such as the projected gelling or clotting time.

The structure and orientation of the apparatus may be of an alternative design and shaping, there may be any number of sections. The sections may be of any shape or structure through which blood or a test fluid could flow. For example, each section could have a uniform cross-sectional area, could have a steadily changing cross-sectional area, or could have a varying cross-sectional area. The number of sections may be varied, in the examples provided there are three sections, however more or less than three sections can also be envisaged. The number of component parts may be varied, in the example, the block containing the channel is illustrated as one component. However, it is preferably divided into sub-components so that the blood-contacting channel is an inexpensive disposable part, whilst the sensing components are not so readily disposable. For example, the channel may be a disposable plastic tube that fits in the channel illustrated in the figures. The block may also divide in the plane illustrated in the figure to provide easy exchange of the disposable part. The apparatus may comprise any suitable material, or combination of materials, of construction.

What is claimed is:

1. A device for determining rheological properties of a non-Newtonian fluid, the device comprising:
a channel, the channel having a plurality of sub-sections, each sub-section having a substantially constant cross-section being provided with a respective differential pressure apparatus for determining a pressure differential across at least a portion of that sub-section, the sub-sections being of different cross-sectional areas;

a first reservoir that is adapted to be located at a first end of the channel and to be placed in fluid communication with the channel, the first reservoir being of variable internal volume;

a second reservoir that is adapted to be placed in fluid communication with first reservoir via the channel, the second reservoir being of variable internal volume;

an inlet for allowing fluid to be introduced into the device;

an outlet, separate to the inlet, at an end of the channel for allowing gas to be substantially eliminated from the device; and an electronically controlled driving element for varying the volume of the first reservoir, such that when the first and second reservoirs are in fluid communication with the first and second ends of the channel respectively, varying the volume of the first reservoir causes fluid to flow along the channel in alternating directions, at pre-determined flow rates in each of the channel sub-sections such that pre-determined strain rates are imposed on the fluid.

2. The device of claim 1, wherein an internal diameter of the at least one sub-section is in a range of 200-2000 micron.

3. The device of claim 1, wherein a length of the at least one sub-section is in a range of 1-15 cm.

4. The device of claim 1, wherein the first and second reservoirs each have a maximum volume that is less than 50 ml.

5. The device of claim 1, wherein one or both of the first and second reservoirs comprises a plunger and a hollow cylinder, the plunger being movable along a longitudinal axis of the cylinder to alter the internal volume of the reservoir.

6. The device of claim 5, wherein one or both of the first and second reservoirs is provided by a syringe.

7. The device of claim 1, wherein one or both of the first and second reservoirs is provided by an elastic body.

8. The device of claim 1, wherein the device comprises a first section including electromechanical parts and associated electronics, and a second section comprising portions for introducing and handling fluid in the device.

9. The device of claim 8, wherein the second section of the device is above, below, within or adjacent the first section and is disposable.

10. A method of measuring the rheological properties of blood, the method comprising:
providing a device according to claim 1;
introducing non-Newtonian fluid into the device;
substantially eliminating gas from the device;
ensuring that the first and second reservoirs are in fluid communication with the channel;
altering the internal volume of the first reservoir so as to cause fluid to flow along the channel in a first direction, between the first and second reservoirs at pre-determined flow rates in each of the channel sub-sections such that pre-determined strain rates are imposed on the fluid;
recording or measuring a rate of fluid flow between the first and second reservoirs;
monitoring the apparatus for determining a pressure differential along at least a portion of the at least one sub-section having substantially uniform cross-section; and
causing the fluid to flow along the channel in a second direction.

11. The method of claim 10, comprising cycling the fluid a plurality of times between the first and second reservoirs.

12. The method of claim 10, further comprising:
tracking changes in rheological behaviour of the fluid as the fluid gels or clots.

13. The method of claim 10, comprising taking measurements in both flow directions and averaging the measurements.

14. The method of claim 10 wherein recording or measuring the rate of fluid flow between the first and second reservoirs comprises using Fourier Transfer, or FFT, signal processing.

15. The method of claim 10, further comprising one of maintaining the device at a controlled temperature or insulating the device to maintain a substantially constant temperature.

* * * * *